United States Patent [19]
Obzansky

[11] Patent Number: 5,369,006
[45] Date of Patent: Nov. 29, 1994

[54] DETERMINATION OF CK ISOENZYMES AND CK ISOFORMS

[75] Inventor: David M. Obzansky, Elkton, Md.

[73] Assignee: E. I. Du Pont de Nemours and Company, Wilmington, Del.

[21] Appl. No.: 752,944

[22] Filed: Aug. 20, 1991

[51] Int. Cl.$^5$ .................. G01N 33/53; G01N 33/551; G01N 33/567; C12Q 1/50

[52] U.S. Cl. .................. 435/7.4; 435/7.92; 435/194; 436/503; 436/524; 436/526

[58] Field of Search .......... 435/7.4, 17.15, 7.9, 435/7.92; 436/548, 536, 539, 541, 524, 525, 528, 811, 532

[56] References Cited

U.S. PATENT DOCUMENTS

| | | | |
|---|---|---|---|
| H622 | 4/1989 | Kageyama | 435/14 |
| 4,231,999 | 11/1980 | Carlsson et al. | 435/7.8 |
| 4,260,678 | 4/1981 | Lepp et al. | 435/7.4 |
| 4,272,506 | 6/1981 | Schwarzberg | 436/512 |
| 4,376,110 | 3/1983 | David et al. | 436/513 |
| 4,387,160 | 6/1983 | Gomez et al. | 435/7.4 |
| 4,624,916 | 11/1986 | Shah et al. | 435/7.4 |
| 4,661,408 | 4/1987 | Lau et al. | 428/405 |
| 4,810,639 | 3/1989 | Pankratz et al. | 435/7.4 |
| 4,912,033 | 3/1990 | Landenson et al. | 435/7.4 |
| 5,236,849 | 8/1993 | Ishikawa | 436/540 |

FOREIGN PATENT DOCUMENTS 0304628  3/1989  European Pat. Off. .

OTHER PUBLICATIONS

Landt, et al. Clin. Chem. 34(3), 1981, pp. 575–581.
Herman, et al. Analytical Biochem. 156, 1986, pp. 48–55.
Vaidya, et al., Clin. Chem., 32(4), 1986, pp. 657–663.
Wu, A. H. B., Clin. Chem., 35/1, 1989 pp. 7–13.
Puleo, et al., Clin. Chem., 35, 1989, pp. 1–4.
Panteghini, M., Clin. Biochem, vol. 21, 1988 pp. 211–218.

*Primary Examiner*—Robert A. Wax
*Assistant Examiner*—Dian C. Jacobson

[57] ABSTRACT

An immunoassay for CK isoenzyme or CK isoform is provided based on capture of the CK isoenzyme or CK isoform by a specific antibody immobilized through a cleavable linker containing a disulfide bond onto a solid phase and release of the resulting antibody-CK isoenzyme or antibody-CK isoform complex by the addition of a reducing agent to cleave the disulfide bond and simultaneously activate the CK isoenzyme or CK isoform.

4 Claims, No Drawings

DETERMINATION OF CK ISOENZYMES AND CK ISOFORMS

TECHNICAL FIELD

This invention relates to the determination of creatine kinase isoenzyme (CK-MB, CK-MM, CK-BB) or creatine kinase isoform (CK-MM1, CK-MM2, CK-MM3, CK-MB1, CK-MB2) levels in a sample via the measurement of activities of antibody-isoenzyme or antibody-isoform complexes. More specifically, CK isoenzyme or CK isoform is immobilized onto a solid phase through the use of CK isoenzyme or CK isoform-specific antibody bound to the solid phase through a clearable linker; such linker is then cleaved by a reducing agent also capable of simultaneously activating the enzymatic activity of the creatine kinase, followed by determination of enzymatic activity of the creatine kinase in solution.

BACKGROUND ART

Three predominant isoenzymes of creatine kinase (CK) are recognized; these are dimers consisting of the M and B sub-units. These dimers may comprise two M or two B sub-units, or one M and one B sub-unit. The predominant dimer present in the blood, serum, or plasma of normal individuals is CK-MM isoenzyme, with variable but usually only trace quantities of CK-MB that indicate the normal degradation of skeletal muscle. The CK-BB isoenzyme is not usually present in detectable amounts in serum of normal individuals but is present in significant quantities in brain tissue and smooth muscle.

Elevations of the CK-BB isoenzyme can occur in pathologic conditions such as metastatic carcinoma or severe burns. The presence of elevated levels of CK-MB isoenzyme has been used as a clinically important indication of myocardial infarction in instances where possible sources of significant skeletal muscle damage can be eliminated. More particularly, repetitive determinations of CK-MB levels in serum can indicate the time course and severity of infarctions. Differentiation between the isoenzymes of creatine kinase, therefore, is clinically important and the availability of a rapid, efficient, and highly discriminatory assay for the CK isoenzymes is needed.

Thrombolytic therapy has become standard care in the treatment of acute myocardial infarction (AMI). To be maximally effective, therapy must be implemented in the initial hours of infarction, so the decision to treat cannot be based upon conventional biochemical markers of AMI, such as total CK and/or CK-MB activities, which may remain within the normal range for six hours or more after the onset of symptoms. Consequently, treatment, which carries some risk of hemorrhage, must be implemented on the basis of clinical and electrocardiographic data, which are of limited diagnostic accuracy in the early hours of AMI. Thus, there are continuing efforts to develop techniques that would more quickly provide a reliable diagnosis.

The isoforms of CK have received recent attention as potential markers for early diagnosis of AMI and for assessing the success of thrombolytic therapy. There are three isoforms of CK-MM; CK-MM1, CK-MM2 and CK-MM3; and two isoforms of CK-MB; CK-MB1 and CK-MB2. The isoforms differ in the presence or absence of a C-terminal lysine residue on the M-subunits of the isoforms. CK-MM3 and CK-MB2, the isoforms present in myocardial tissue, have a C-terminal lysine residue on each M-subunit of the isoform. After AMI, CK-MM and CK-MB are released from injured myocardium into plasma. Over time, the myocardial tissue isoforms convert to the plasma isoforms. CK-MM3 first converts to CK-MM2 which, in turn, converts to CK-MM1 and CK-MB2 converts to CK-MB1. The conversion occurs as plasma carboxypeptidase cleaves the C-terminal lysine residues from the M-subunits. Shortly following AMI, the ratio of the tissue isoforms of CK-MM and CK-MB to the plasma isoforms increases. Such increase occurs several hours before either total CK or CK-MB activity exceeds normal reference levels.

Several approaches to analysis of CK isoenzymes and isoforms have been used which rely either upon physical separation of the isoenzymes or isoforms with subsequent identification, or upon highly selective reactions between the isoenzymes or isoforms and antibodies. Physical separation methods such as electrophoresis or column chromatography are time consuming, require considerable skill, and are frequently incapable of highly reproducible separations to resolve adequately the isoenzymes with sufficient sensitivity to monitor early changes in CK-MB levels. The inconvenience of physical separation techniques and their inability to unequivocally resolve CK isoenzymes lead to immunochemical techniques which, based upon their unique structural or immunochemical determinants, have the potential to differentiate between the isoenzymes in complex mixtures.

U.S. Pat. No. 4,260,678, issued Apr. 7, 1981 to Lepp et al., discloses a CK assay using immobilized antibodies to either the CK-M or CK-B sub-unit, or both. The selected antibody, which did not inhibit or substantially change the activity of the bound sub-unit, was immobilized on a carrier such as porous glass beads and then reacted with sample followed by the separation of the immobilized antibody-isoenzyme complexes from the reaction mixture prior to the determination of enzyme activity of sub-units bound to the carrier. This approach is useful to determine total activity by reacting both anti-CK-M and anti-CK-B carriers with sample, or of individual sub-units by reaction of one or the other carrier with sample. It is not possible to determine the activity associated with the hybrid dimer CK-MB or CK isoforms using this approach.

U.S. Pat. No. 4,387,160, issued Jun. 3, 1983 to Gomez et al., discloses an assay for CK-MB which uses three separate antibody preparations and two separate assays on a given sample. In one assay, a precipitating anti-CK-M antibody capable of substantially or completely inhibiting the M-subunit activity, without significantly affecting B-sub-unit activity, is combined with one portion of a sample and allowed to react. If precipitation occurs during this reaction, the precipitate will remain homogeneously suspended during the process of this reaction. The residual isoenzyme activity in this solution is determined by conventional means. A second portion of sample containing at least CK-M sub-units is reacted with an anti-CK-M antibody and the complexes so formed are further reacted with a precipitating second antibody capable of reacting with determinants on the anti-CK-M antibody. The precipitate is separated from the reaction mixture and residual activity, presumably representing B sub-unit remaining in the supernatant, is determined by conventional means. Activity from the second sample representing contaminating B sub-units is subtracted from the activity of the first sample, which represents both MB and contaminating B sub-units, to determine MB activity. This assay combines immunoinhibition with precipitation techniques to determine CK-MB levels in samples, but does so with considerable inconvenience in time-consuming processing steps and with several, highly specialized reagents.

Sandwich immunoassays employing the two-site immunometric approach to measure mass concentrations have been used to detect CK-MB by immobilizing either all M or all B-containing sub-units onto a solid phase through an antibody specific for that sub-unit attached to the solid phase (see U.S. Pat. No. 4,376,110, issued Mar. 8, 1983 to Davis et al., and U.S. Pat. No. 4,624,916, issued Nov. 25, 1986 to Shah et al.). The immobilized sub-unit is then detected by a labelled second monoclonal antibody specific for that sub-unit. The amount of label detected is a direct measure of the desired sub-unit in the original sample. This approach requires two highly specific reagents and is subject to an elevated number of false positive results due to the nonspecific binding of the labelled antibody to the solid phase.

Landt et al., Clin. Chem., 34(3): 575–581 (1981), disclose a colorimetric assay for CK-MB isoenzyme which is a modification of a previously published method [Vaidya et al., Clin. Chem., 32: 657–663 (1986)] based on the use of a monoclonal antibody specific for the CK-MB isoenzyme. Polystyrene beads were coated with the CK-MB-specific monoclonal antibody and then mixed with a serum sample to extract CK-MB. The beads were washed to remove unbound CK isoenzymes and measured for bound CK-MB activity. This method is limited to the determination of CK-MB isoenzyme and cannot be used for the CK isoforms. Furthermore, this technique is not useful in automated analyzers which are limited to the analysis of enzymes in free solution.

U.S. Pat. 4,810,639, issued Mar. 7, 1989 to Pankratz, discloses an immunoassay for CK-MB based on sequential immunoinhibition first by an immobilized and then by a soluble antibody of either the CK-M or CK-B subunits of CK-MM, CK-MB, and CK-BB, followed by an enzymatic determination of the unbound sub-unit in CK-MB; the unbound CK-BB or CK-MM having been previously removed. It is not possible to determine the activity associated with the CK isoforms using this method.

The techniques mentioned thus far are applicable only to the analysis of CK-MB isoenzyme and do not provide for the determination of CK isoforms; thus they have limited utility in the early diagnosis of AMI, when either total CK or CK-MB activity is still within the normal reference range.

Puleo et al., Clin. Chem., 35: 1–4 (1989), disclose an assay based on high voltage gel electrophoresis which can quantitatively determine CK-MB isoforms in plasma at activities as low as 1.25 U/L. This method is of limited utility in a clinical setting due to shortcomings associated with physical separation methods such as lack of reproducibility and the high level of skill required for successful completion.

European Patent application Publication Number 304,628, published on Mar. 1, 1989, discloses an immunoassay for determining the levels of CK-MM$_A$ (CK-MM1), CK-MM$_B$ (CK-MM2), and CK-MM$_A$ and CK-MM$_B$ combined, using antibodies specific for the two isoforms and an antibody selective for both the CK-MM$_A$ and CK-MM$_B$ isoforms but not CK-MB or the CK-MB isoforms. An immunoassay is described which includes immobilization of a selected antibody onto an insoluble solid support, incubation of the antibody-coated support with sample to allow for extraction of the isoform of interest, and, finally, determination of the isoform while bound to the support. Other formats, including sandwich immunoassays and competitive schemes, are also described. This method is not useful for the determination of total CK-MB or the CK isoforms in automated analyzers which are limited to the analysis of enzymes in free solution.

U.S. Pat. No. 4,231,999, issued Nov. 4, 1980 to Carlsson et al., discloses a method for carrying out immunoassays based on the formation of an insoluble conjugate having incorporated into it an analytically indicatable group which is subsequently separated as part of a fragment of the conjugate and assayed in the liquid phase. Fragments containing the analytically indicatable group are formed by splitting the insoluble conjugate at bonds that are covalent in nature, where the splitting of such bonds does not reduce the activity of the analytically determinable group or damage a reagent that comprises a labelled immunochemical component.

Thus, this method requires the use of a labelled reagent. Additionally, since this immunoassay measures the amount of label in solution, the measurement is really one of mass concentration rather than direct activity of the desired analyte. There is some debate as to whether mass measurement is as accurate as CK activity measurement in determining actual CK-MB isoenzyme or CK isoform content.

There is a need for a rapid CK isoenzyme and CK isoform assay that can provide precisely and economically an accurate evaluation of CK isoenzyme or CK isoform levels in body fluids of an individual suspected of suffering from acute myocardial infarction. Further, there is a need for a CK isoenzyme and CK isoform assay that is useful with automated analyzers which are limited to the analyses in free solution.

DISCLOSURE OF THE INVENTION

The CK isoenzyme or CK isoform immunoassay of this invention comprises:

(a) immobilizing an antibody specific for CK isoenzyme or CK isoform onto a solid phase through a cleavable linker containing a disulfide bond;

(b) contacting the immobilized antibody with a sample containing CK isoenzyme or CK isoform to form immobilized antibody-CK isoenzyme or antibody-CK isoform complex;

(c) separating the immobilized complex formed in step (b) from soluble components;

(d) releasing antibody-CK isoenzyme or antibody CK-isoform complex from the solid phase by contacting the immobilized complex with a reducing agent capable of cleaving the disulfide bond of the clearable linker and simultaneously activating the CK isoenzyme or CK isoform enzymatic activity;

(e) separating the solid phase from the released antibody-CK isoenzyme or antibody-CK isoform complex; and (f) determining the enzymatic activity of CK isoenzyme or CK isoform in solution.

DESCRIPTION OF THE INVENTION

The method of this invention is capable of determining specifically the enzymatic activity of CK isoenzyme and CK isoform levels in liquid samples through the measurement of activities of antibody-isoenzyme or antibody-isoform complexes in a rapid, simple, efficient, and economical manner. Liquid samples include whole blood, serum, plasma, cerebrospinal fluid, urine, pleural and lymphatic fluids, and any other biological fluid suspected of containing CK isoenzymes or CK isoforms.

An important aspect of this invention is the preparation of an appropriate anti-CK isoenzyme or anti-CK isoform antibody, which is capable of binding with CK isoenzymes or CK isoforms and which will not substantially affect the enzymatic activity of the CK isoenzyme or CK isoform bound to the antibody.

These antibodies can be obtained by known methods. For example, the crystallized CK isoform antigens from skeletal muscle tissue of vertebrates, preferably those of human origin, are inoculated into an immunocompetent host according to an appropriate schedule which causes the amount of circulating antibodies reactive with the antigen to increase. Antigen sources may be selected from skeletal muscles of various animals such as pigs, sheep, cattle, horses, donkeys, rabbits, and guinea pigs. Other animals such as rats, mice, and birds can also be used. The immune serum can be harvested and used directly following appropriate activity determinations, or antibodies can be purified from animal serum by known methods. The purified antibodies can be used whole, or can be fragmented by enzyme digestion using papain, pepsin, etc., to produce monovalent or divalent partial antibodies, respectively. Alternatively, immune lymphocytes can be obtained from the host animal and when these lymphocytes are fused with appropriate immortal cells, such as myeloma cells, they will produce hybridoma cells capable of secreting desired monoclonal antibodies. These techniques are familiar to one skilled in the art; a more complete description can be found in Mayer et al., Immunochemical Methods In The Biological Sciences: Enzymes and Proteins, Academic Press, London, 1980, p. 5-17. A suitable anti-CK-MB isoenzyme antibody has been described by Vaidya et al., Clin. Chem., 32(4):657-663 (1986), incorporated herein by reference, and will hereinafter be referred to as the "Conan antibody".

The particular animal source, antibody isotype, and whether whole or partial antibody is used are not critical in the carrying out of the method of this invention as long as certain criteria are met. The selected antibody must be capable of binding to CK isoenzyme or CK isoform and remain associated with it through several washing procedures. This requirement is most readily met by those antibodies with affinity constants at least $10^6$ liters/mole, preferably $10^7$ liters/mole, and most preferably $10^9$ liters/mole.

The immobilization procedure for attaching antibody to an appropriate solid phase needs to be selected carefully. The procedure should be sufficiently mild to preserve the binding abilities of the antibody in reactions with the CK isoenzyme or isoform, but result in a stable product to withstand the immunoassay conditions. The immobilization procedure of this invention includes attaching the antibody to the solid phase through a cleavable linker. By clearable linker is meant a chemical bridge, which contains a disulfide (—S—S—) bond, between the solid support and the antibody The clearable linker can be formed between the solid support and the antibody through covalent or non-covalent binding. Non-covalent binding can be achieved through streptavidin-biotin or avidin-biotin coupling. For example, streptavidin can be attached to chromium dioxide ($CrO_2$) particles and reacted with biotinylated anti-CK isoenzyme antibody containing a disulfide bond between the antibody and the biotin, to produce a $CrO_2$ particle-streptavidin-biotin-S-S-anti-CK isoenzyme antibody complex. Alternatively, covalent binding of the cleavable linker can be achieved using solid phases having surface functional groups such as epoxy, imino, amino, carboxyl, aryl, halosulfonyl, sulfhydryl, which can react with homo- or hetero-bifunctional reagents.

Any homo- or hetero-bifunctional reagent which is capable of forming a disulfide bond between the solid support and anti-CK isoenzyme or anti-CK isoform antibody can be used to form the cleavable linker. These bifunctional reagents can be reacted with the desired anti-CK isoenzyme antibody or anti-CK isoform antibody before or after exposure to the solid phase. Examples of reagents which can be used to form the disulfide bonds of the clearable linkers of this invention include pyridyl disulfides that react with -SH groups to form a disulfide bond, sulfosuccinimidyl 2-(m-azido-o-nitrobenzamido)-ethyl-1,3'-dithiopropionate (SAND), N-succinimidyl(4-azidophenyl)1,3'-dithiopropionate (SADP), sulfosuccinimidyl(4-azidophenyl-dithio)proprionate (Sulfo-SADP), sulfosuccinimidyl 2-(biotinamido)ethyl-1,3-dithiopropionate (NHS-SS-Biotin), N-succinimidyl 3-(2-pyridyldithio)propionate (SPDP), dithiobis(succinimidyl-propionate) (DSP), and N-(2-pyridyldithio propionyl) biocytin (PDP-Biocytin). The preferred reagent is PDP-Biocytin.

A single reagent containing a disulfide bond can be used or alternatively, the disulfide bond can be introduced through the use of two reagents, where each reagent contributes to the formation of the disulfide bond. For example, N-succinimidyl-s-acetylthioacetate (SATA) and N-succinimidyl 3-(2-pyridylthio)propionate (SPDP) can be used to introduce a free sulfhydryl group onto an anti-CK isoenzyme antibody or anti-CK isoform antibody. The thiolated anti-CK isoenzyme or anti-CK isoform antibody can then be reacted with a reagent, such as PDP-Biocytin, which reacts with the sulfhydryl group of the thiolated antibody to form a disulfide bond.

A reducing agent is any reagent which is capable of cleaving the disulfide bond of the clearable linker while simultaneously activating CK isoenzyme or CK isoform enzymatic activity. Examples of such reducing agents include N-acetyl cysteine (NAC), betathioglycerol (BTG), beta-mercaptoethanol (BME), dithiothreitol (DTT), dithioerythritol (DTE) and glutathione (GSH). The preferred reducing agent is DTT.

The solid phase on which the antibody is immobilized can be organic or inorganic, porous or non-porous and in any desired shape or form. The solid phase can be particulate having its physical properties, such as density, surface area and diameter, selected to meet the needs of a particular assay application. Particles which require large amounts of attached antibody, and which must be in maximum contact with antigen in reaction mixtures over extended periods, can be selected from those particles which have large surface area to volume ratios, accessible, reactive functional groups for antibody attachment, and densities approaching that of the suspending medium to prevent settling. Small particle diameters, to provide a high surface area per volume of particulate reagent dispensed, are preferred. Alternatively, the solid phase can be shaped in any desired form such as in flat sheets, cylindrical shafts, circular wafers, or rectangular or cuboidal blocks to conform with specifications of manual or automated systems which are designed to move reaction mixtures into and out of contact with the solid phase. The solid phase can have any desired size, shape, porosity, texture, density, and composition, selected from a wide variety of known materials to suit the specific assay configuration. For example, both controlled pore hollow fiber bundles of polysulfone or porous high density polyethylene rods (available from Porex® Technologies Inc., Fairburn, Ga.) can be used conveniently for the immobilization of antibodies and would also provide acceptable physical properties.

Inorganic solid phases can include silaceous materials such as glass, silica, bentonite, and metal oxides of iron, nickel, titanium, chromium, etc. One particular advantage of selected metal oxides of iron and chromium is their magnetic properties that allow magnetic separations of solid phases from reaction mixtures. These magnetic properties can be ferromagnetic and paramagnetic. Each of these solid phases can be treated by known methods to coat their surfaces for linking proteins, see for example U.S. Pat. No. 3,652,761, issued Mar. 28, 1972 to Weetall et al., incorporated herein by reference. Silaceous hydroxyl groups can be silanized by a variety of agents having groups capable of forming amide, ester, ether, disulfide, and sulfonamide linkages with antibody.

A preferred solid phase for use in the present invention is the surface stabilized (protected) chromium dioxide ($CrO_2$) particles described in U.S. Pat. No. 4,661,408, issued Apr. 28, 1987 to Lau et al., incorporated herein by reference.

The protected $CrO_2$ particles have the properties of low remnant magnetism and favorable surface structure which allows for repeated magnetic separation and dispersion cycles; rapid separation in a magnetic field; high surface area for high capture capacity; and a highly stable particle for maximum reagent shelf life.

The magnetic particles are sufficiently hydrolytically stable to be useful as solid supports in heterogeneous immunoassays and bioaffinity separations. The core of the particles is acicular, rutile chromium dioxide. This material and its preparation is described in U.S. Pat. Nos. 2,923,683, 4,524,008, and 3,512,930, which are incorporated herein by reference. The chromium dioxide particles have a surface area of 5–100 $m^2/g$, coercivity of 100–750 oersteds, remanent magnetization of 5–45 emu/g and saturation magnetism of 8–85 emu/g. These particles are surface stabilized as taught in U.S. Pat. No. 3,512,930. The stabilized surface layer is characterized by its X-ray diffraction pattern which exhibits a line corresponding to an interplanar spacing of 316.8 pm.

The chromium dioxide particles are further stabilized with a coating of $SiO_2$. The weight of $SiO_2$ coating the particles is greater than about 1% and preferably from 2–6% of the weight of the chromium dioxide. The silica coated chromium dioxide is then further coated with a silane to both further stabilize the particle and to provide binding sites for proteins. The choice of silane is dictated by the need to bind proteins to the magnetic particles, and a wide variety of such compounds are available. The magnetic particle when coated with silica and silanized has a particle size of 0.5 to 5 $\mu m$ and a remanent magnetization of 8 to 21 emu.

The immunoassay of the present invention is a heterogeneous immunoassay performed by immobilizing anti-CK isoenzyme or anti-CK isoform antibodies onto a solid phase through a cleavable linker, contacting the immobilized antibody with sample containing CK isoenzyme or CK isoform to form immobilized antibody-CK isoenzyme or antibody-CK isoform complex, releasing antibody-CK isoenzyme or antibody-CK isoform complex from the solid phase by contacting the immobilized antibody-CK isoenzyme or antibody-CK isoform complex with a reducing agent capable of breaking the cleavable linker and simultaneously activating the enzymatic activity of the CK isoenzyme or CK isoform, and measuring the enzymatic activity of the released CK isoenzyme or CK isoform in solution.

A sample containing a mixture of CK isoenzymes and CK isoforms is contacted with a solid phase having immobilized thereon an antibody specific for the CK isoenzyme or CK isoform of interest for a time sufficient to allow the formation of immobilized antibody-CK isoenzyme or antibody-CK isoform complex to occur. The solid phase containing the immobilized antibody-CK isoenzyme or antibody-CK isoform is washed an appropriate number of times to insure removal of unbound isoenzymes, isoforms, and other contaminants, such as mitochondiral CK, IgG bound CK or "atypical CK", adenylate kinase, etc. Antibody-CK isoenzyme or antibody-CK isoform complex is removed from the solid phase by contact with a reducing agent that breaks the disulfide bond of the cleavable linker and simultaneously activates the CK isoenzyme or CK isoform.

Specifically, the sample suspected of containing CK isoenzyme or CK isoform is contacted with a solid phase bearing anti-CK isoenzyme or anti-CK isoform antibody and the mixture is allowed to react for from one minute to one hour, preferably from 5 to 30 min, at between 5° C. to 50° C., preferably from 25° C. to 40° C., to insure that a portion of the CK isoenzyme or the specific CK isoform to be determined in the sample forms a complex with the immobilized anti-CK isoenzyme antibody or the specific CK isoform antibody.

The solid phase containing immobilized antibody-CK isoenzyme or antibody-CK isoform complex can be separated from soluble components by any convenient means, such as centrifugation, filtration and magnetic or chromatograhic separation, followed by washing with buffer to remove sample constituents and contaminants not bound to the solid phase. Magnetic separation is the preferred method of separation. The washed solid phase is then contacted with a reducing agent and the mixture is allowed to react for from 0.1 min to 1 hr, preferably from 5 to 30 min, at between 5° C. to 50° C., preferably from 25° C. to 40° C., to insure that the antibody-CK isoenzyme or antibody-CK isoform complex has been released from the solid phase. The solution containing released antibody-CK isoenzyme or antibody-CK isoform complex is then contacted with an appropriate substrate for the determination of CK activity. The substrate is selected to produce a detectable signal and can be chromogenic, fluorogenic, chemiluminogenic, etc. The detectable signal can be produced directly by the CK activity on the substrate, or indirectly by the activity of other reagents that depend for their activity upon the activity of CK isoenzyme or CK isoform. These substrate reagents are known and are described in detail in U.S. Pat. No. 4,260,678, issued Apr. 7, 1981 to Lepp et al.

The preferred method for measuring the enzymatic CK isoenzyme or isoform activity is a coupled enzymatic reaction whereby CK catalyzes the transphorylation of phosphate from creatine phosphate to adenosine diphosphate (ADP) producing adenosine triphosphate (ATP). The ATP thus formed phosphorylates glucose in a reaction catalyzed by hexokinase and the resulting glucose-6-phospate is oxidized by glucose-6-phospate dehydrogenase (G6PDH) with simultaneous reduction of nicotinamide adenine dinucleotide phosphate (NADP). The rate of production of the reduced form of NADP is then related to the CK activity.

Among the advantages realized by the immunoassay of this invention are the removal of contaminating CK isoenzymes (mitochondrial CK, IgG bound CK or "atypical CK") and other enzymes, such as adenylate kinase, present in biological samples which are capable of interfering in the enzymatic determination of CK isoenzyme or CK isoform activity. Also, any contribution to the enzymatic activity of any CK isoenzyme during the assay from the other CK isoenzymes or CK isoforms other than the bound isoform is eliminated. The immunoassay of the present invention allows for the determination of CK isoforms based on using antibodies specific for the CK isoform to be determined. Further, the assay of the present invention can be performed with an automated instrument which is limited to analyses in free solution.

The following example illustrates the invention:

EXAMPLE

I. Preparation of $CrO_2$ Particles Containing Immobilized anti-CK-MB

A. Reductive Surface Treatment of Chromium Dioxide ($CrO_2$) Particles

The solid phase was prepared using chromium dioxide magnetic particles available from E. I. du Pont de Nemours and Company, Wilmington, DE. 600 g of upgraded heated chromium dioxide particles were mixed with 360 g of sodium bisulfite in 6000 mL of water and the mixture was milled for 72 hr. The milled particles were dialyzed against 120 l of distilled water to remove excess sodium bisulfite.

B. Silica Coating

To stabilize the core particles against reoxidation, a silica coating was deposited on the $CrO_2$ particles according to the following procedure.

12 l of $CrO_2$ particles prepared according to step A above were heated to 90° C. $\pm 2°$ C. in a 22 l flask with mechanical stirring. 6 g of sodium bisulfite and 7.17 g of sodium aluminate were added to this mixture, and the pH of the suspension was adjusted to 9.0. 1000 ml of water containing 150 g of sodium metasilicate and 37.5 g of sodium metaborate were then added dropwise over a period of 1 hr. During this period, the pH of the mixture was maintained at 9.0 $\pm 0.2$ by the simultaneous dropwise addition of 1.0N sulfuric acid. Vigorous stirring was maintained throughout the reaction. The mixture was heated to 90° C. and stirred for an additional 30 min. The mixture was then cooled to 50° C. and diluted with purified water to 24 l. Following this, the mixture containing silica-coated $CrO_2$ particles was dialyzed against 150 l of purified water and concentrated to 10.8 l.

C. Silane Coating

The particles prepared in step B above were transferred to a 22 l round-bottom flask equipped with a mechanical stirrer, a reflux condenser, and a temperature sensor. 1200 mL of aminopropyltriethoxy-silane were added and the mixture stirred at 55° C. for 18 hr. The mixture was then cooled to 50° C., diluted to 24 l with purified water, and dialyzed against 150 l of purified water. Following this, the particles were resuspended in 11.2 l of a solution containing 16.56 g sodium phosphate monobasic and 0.24 g thimerosal and having a pH of 7.1. The $CrO_2$ particles thus prepared were found to contain 4.89% $CrO_2$ by weight and were characterized by a settling time of approximately 12 min, particle size of approximately 1.58 microns, and magnetic separation time of approximately 53 sec.

D. Streptavidin-containing $CrO_2$ Particles 1000 mL of silanized $CrO_2$ particle slurry prepared in step C above were washed with 4000 mL of 10 mM potassium phosphate buffer, pH 7.0. 400 mL of 25% glutaraldehyde, which had been diluted to 1000 mL with 10 mM potassium phosphate buffer, pH 7.0, were slowly added to the 1000 mL of the washed silanized $CrO_2$ particle slurry and the solution was mixed for 3 hr at room temperature. The resulting glutaraldehyde-activated $CrO_2$ particles were then washed with 10 mM potassium phosphate, pH 7.0, and concentrated to 800 mL.

To prepare the streptavidin-containing $CrO_2$ particles, 750 mL of the glutaraldehyde-activated $CrO_2$ particles were added to 1500 mg of streptavidin in 750 mL of 10 mM potassium phosphate buffer, pH 7.0, and the slurry was mixed for 16 hr at 40° C. Unreacted aldehyde groups were then quenched by reaction with 4500 mL of 2M glycine, pH 9.0, for 1 hr. The resulting streptavidin-containing $CrO_2$ particles were washed extensively with 10 mM potassium phosphate buffer, pH 7.0, to remove all noncovalently bound material. The particles were concentrated to 1200 mL and 1.5 g bovine serum albumin (BSA) and 0.15 g thimerosal were added. The mixture containing the streptavidin-containing $CrO_2$ particles was then diluted to 1500 mL with 10 mM potassium phosphate buffer, pH 7.0. The streptavidin-containing $CrO_2$ particle reagent thus prepared was found to contain 2.3% $CrO_2$ by weight and was characterized by an average particle size of approximately 1.6 microns, and magnetic separation time of approximately 31 sec.

E. Streptavidin-$CrO_2$ Tablets

The streptavidin-containing $CrO_2$ particle reagent prepared in step D above was incorporated into tablets using a spray/freeze/lyophilization process disclosed in U.S. Pat. No. 3,721,725, issued Mar. 20, 1973 to Briggs et al., to prepare the blend and conventional techniques to prepare 14 mg tablets. Each 14 mg tablet thus prepared contained 3.0 mg $CrO_2$ containing streptavidin, 0.98 mg carbowax, 0.012 mg thimerosal, 8.8 mg trehalose, 0.9 mg 2chloroacetamide, and 0.3 mg nonspecific rabbit IgG.

F. Biotinylation Of Anti-CK-MB Antibody

The anti-CK-MB antibody used was the "Conan antibody" disclosed by Vaidya et al., Clin. Chem., 32:657–663 (1986) and incorporated herein by reference. The "Conan antibody" is specific for the CK-MB isoenzyme and does not cross-react with CK-MM or CK-BB. N-(2-pyridyldithio-propionyl) biocytin (PDP--Biocytin; Calbiochem Corporation) was used to biotinylate the anti-CK-MB antibody.

5 mL of a solution containing 4.4 mg/mL anti-CK-MB antibody in 10 mM sodium phosphate, 300 mM sodium chloride, and 0.02% sodium azide were dialyzed against 800 mL of an antibody dialysis buffer containing 10 mM sodium phosphate and 300 mM sodium chloride to remove the azide from the antibody solution. Following dialysis, 109 nmoles of anti-CK-MB antibody was thiolated by reaction with 1633 nmoles of N-succinimidyl 3-(2pyridyldithio) propionate (SPDP; Pierce Chemical Co.) and then reduced with 100 mM dithiothreitol (DTT; Pierce Chemical Co.). The thiolated anti-CK-MB antibody was then separated from DTT using a G-25 gel filtration column (Pharmacia Co.).

Two preparations of biotinylated anti-CK-MB antibody, A and B, were made as follows. Preparation A contained a 3:1 molar ratio of PDP-Biocytin:IgG. Approximately 45 nmoles of thiolated anti-CK-MB antibody was reacted with 134 nmoles of PDP-Biocytin. Preparation B contained a 5:1 molar ratio of PDP-Biocytin:IgG. Approximately 45 nmoles of thiolated anti-CK-MB antibody was reacted with 223 nmoles PDP-Biocytin. For both the A and B preparations, the reaction was allowed to proceed for 60 min and was followed by isolation of the biotinylated anti-CK-MB antibody using a G-25 gel filtration column (Pharmacia Co.).

G. Immobilization of anti-CK-MB Antibody onto $CrO_2$ Particles $CrO_2$ particles containing anti-CK-MB antibody attached through a cleavable linker were prepared by reacting streptavidin-containing $CrO_2$ particles with the biotinylated anti-CK-MB antibody prepared in step F above. The structure of the resulting complex was as follows: $CrO_2$ Particle-streptavidin-biotin-S-S-anti-CK-MB antibody.

Streptavidin tablets were hydrated with 1 mL $H_2O$ each in polypropylene test tubes. Following magnetic separation the supernatant was discarded. 1 mL of 20 mM tris buffer (pH 7.2) was added to each tube followed by varying amounts (0 to 1.0 mL per tube) of biotinylated anti-CK-MB antibody. One set of tubes was prepared for each of Preparation A and B of biotinylated anti-CK-MB antibody. Binding of biotinylated anti-CK-MB antibody to $CrO_2$ particles was allowed to proceed for 23 min with intermittent mixing using a vortex mixer. The resulting particles were washed four times (2.0 mL per wash) with 20 mM tris buffer (pH 7.2).

II. Determination Of CK-MB Isoenzyme Captured

To each tube containing $CrO_2$ particle having anti-CK-MB antibody immobilized thereon was added 0.1 mL of sample containing CK-MB. Following incubation, the particles were magnetically separated from soluble components and the activity of total CK in the supernatant determined using the Cobas Bio TM (Roche Diagnostics) and reagents for the determination of CK (CK-NAC; Boehringer Mannheim Diagnostics). The results are shown in Table 1.

TABLE 1

| Volume of Biotinylated anti-CK-MB antibody (μL) | Biotinylated Preparation (U/L) | CK Activity | Percent Capture* |
| --- | --- | --- | --- |
| 0 | | 333 | 0 |
| 10 | A | 123 | 63 |
| 100 | A | 89 | 73 |
| 1000 | A | 118 | 65 |
| 10 | B | 101 | 70 |
| 100 | B | 56 | 83 |

TABLE 1-continued

| Volume of Biotinylated anti-CK-MB antibody (μL) | Biotinylated Preparation (U/L) | CK Activity | Percent Capture* |
| --- | --- | --- | --- |
| 1000 | B | 69 | 79 |

*Percent Captured =
$100 \times \frac{\text{CK Activity (at 0 Antibody)} - \text{CK Activity (at test point)}}{\text{CK Activity (at 0 antibody)}}$ The results show that the biotinylated anti-CK-MB was attached to the $CRO_2$ particles; that the particles efficiently bound CK-MB from the sample; and that up to 83% of the CK-MB was bound.

III. Release of CK-MB Isoenzyme from Solid Phase

To each of 10 tubes containing 3 streptavidin-containing $CrO_2$ particle tablets was added 0.3 mL of biotinylated anti-CK-MB antibody (Preparation B). The tablets were dissolved into particles by addition of the antibody. These tubes were incubated for 30 min at room temperature with occasional mixing using a vortex mixer. The particles were magnetically separated and the supernatant discarded. Particles were then washed five times with 1.0 mL of 20 mM Tris buffer (pH 7.2). Samples (0.5 mL) containing CK-MB were added to each tube. After 8 min of incubation, percent capture of the CK-MB onto the solid phase was determined according to the procedure described in Section II. Approximately 90% of the CK-MB had been captured onto the solid phase. The tubes were washed three times with 1.0 mL of 20 mM Tris buffer (pH 7.2). ½ mL of freshly prepared solution of 258 mM DTT in 20 mM tris buffer (pH 7.2) was added to each tube. At 6, 8, 45, and 63 min, the particles were separated and the supernatant analyzed for CK activity using the Cobas Bio TM (Roche Diagnostics) and reagents for the determination of CK (CK-NAC; Boehringer Mannheim Diagnostics). The results are shown in Table 2.

TABLE 2

| Time (minutes) | Observed CK Activity (U/L) | Corrected CK Activity (U/L) | Percent Released |
| --- | --- | --- | --- |
| 6 | 39 | 21 | 13 |
| 8 | 58 | 31 | 19 |
| 45 | 91 | 49 | 30 |
| 63 | 92 | 50 | 31 |

Control experiments were performed which indicated that 258 mM DTT increases CK activity by a factor of 1.85. Therefore the "corrected CK activity" in Table 2 is determined by dividing the observed CK activity by 1.85. The percent released in Table 2 was calculated by dividing the "corrected CK activity" by the amount of CK-MB captured (161 U/L) and multiplying by 100.

The results indicate that by using a reducing agent capable of activating CK-MB enzymatic activity and simultaneously cleaving the disulfide bond of the clearable linker, up to 30% of the CK-MB activity could be released from the particles.

IV. Calibration Curve For Specific CK-MB Assay

To each of 10 tubes containing 2 streptavidin-containing $CrO_2$ tablets was added 0.13 mL of a 1:1 dilution of biotinylated anti-CK-MB antibody (Preparation A) and 20 mM tris buffer (pH 7.2). The tablets were dissolved into particles upon the addition of the antibody and buffer. The particles were incubated for 15 minutes at room temperature with occasional mixing using a vortex mixer. The particles were washed five times with 0.5 mL of 20 mM tris buffer (pH 7.2).

The washed particles were incubated with 0.3 mL of each of five levels of CK-MB calibrator for 5 min. The particles were magnetically separated and the supernatant discarded. Following separation, the particles were washed twice with 0.3 mL of a 20 mM tris buffer (pH 7.2). To each tube, 0.3 mL of freshly prepared 258 mM DTT in 20 mM tris buffer (pH=7.2) was added followed by incubation at room temperature and mixing using a vortex mixer for 30 min. The particles were magnetically separated and the supernatant tested for CK activity. The activity of the calibrators was measured before and after the binding and release steps using the Cobas Bio ™ CK activity assay directly. The results are shown in Table 3.

TABLE 3

| CK Activity | |
|---|---|
| Before (U/L) | After (U/L) |
| 1.72 | 0.29 |
| 5.16 | 9.19 |
| 8.44 | 16.76 |
| 36.73 | 84.25 |
| 57.08 | 150.60 |

Correlation statistics for Table 3 are as follows: slope = 2.66, intercept = −5.78, r = 0.997.

Table 3 demonstrates a standard curve prepared using the heterogeneous immunoassay of the instant invention wherein capture antibody is attached to a solid phase through a clearable linker containing a disulfide bond and the activity of antibody-captured CK-MB is measured after the simultaneous cleaving of the disulfide bond of the cleavable linker and activation of the CK-MB enzymatic activity by a reducing agent. The higher activity exhibited by the calibrator after the release step facilitates measurement of CK-MB activity.

What is claimed is:

1. A heterogeneous immunoassay for the measurement of CK isoenzyme or CK isoform in a liquid sample comprising the steps of:
    (a) immobilizing an antibody specific for CK isoenzyme or CK isoform onto a solid phase through a cleavable linker containing a disulfide bond;
    (b) contacting the immobilized antibody with a sample containing CK isoenzyme or CK isoform to form immobilized antibody-CK isoenzyme or antibody-CK isoform complex;
    (c) separating the immobilized complex formed in step (b) from soluble components;
    (d) releasing antibody-CK isoenzyme or antibody CK-isoform complex from the solid phase by contacting the immobilized complex with a reducing agent capable of cleaving the disulfide bond of the clearable linker and simultaneously activating the CK isoenzyme or CK isoform enzymatic activity;
    (e) separating the solid phase from the released antibody-CK isoenzyme or antibody-CK isoform complex; and
    (f) determining the enzymatic activity of CK isoenzyme or CK isoform in solution.

2. The heterogeneous immunoassay of claim 1, wherein the CK isoenzyme is CK-MB.

3. The heterogeneous immunoassay of claim 1, wherein the solid phase is chromium dioxide particles.

4. The heterogeneous immunoassay of claim 1, wherein the reducing agent is dithiothreitol.

* * * * *